United States Patent
Liphardt et al.

(10) Patent No.: US 8,248,606 B1
(45) Date of Patent: Aug. 21, 2012

(54) SAMPLE MAPPING IN ENVIRONMENTAL CHAMBER

(75) Inventors: Martin M. Liphardt, Lincoln, NE (US); Blaine D. Johs, Lincoln, NE (US)

(73) Assignee: J.A. Woollam Co., Inc., Lincoln, NE (US)

(*) Notice: Subject to any disclaimer, the term of this patent is extended or adjusted under 35 U.S.C. 154(b) by 459 days.

(21) Appl. No.: 12/584,794

(22) Filed: Sep. 12, 2009

Related U.S. Application Data

(60) Provisional application No. 61/191,970, filed on Sep. 15, 2008.

(51) Int. Cl.
*G01J 4/00* (2006.01)
(52) U.S. Cl. .......................... 356/369; 356/439; 356/440
(58) Field of Classification Search .................. 356/638, 356/639, 640, 437–439
See application file for complete search history.

(56) References Cited

U.S. PATENT DOCUMENTS

| | | | |
|---|---|---|---|
| RE38,153 E | 6/2003 | Finarov | 356/630 |
| 6,687,002 B2 | 2/2004 | Stehle et al. | 356/369 |
| 6,937,341 B1 | 8/2005 | Woollam et al. | 356/436 |
| 6,970,532 B2* | 11/2005 | Hayashi et al. | 378/79 |
| 7,120,228 B2* | 10/2006 | Yokhin et al. | 378/90 |
| 7,238,234 B2* | 7/2007 | Bae et al. | 118/302 |
| 2002/0075486 A1* | 6/2002 | Zhang et al. | 356/630 |
| 2006/0165873 A1* | 7/2006 | Rueger et al. | 427/8 |
| 2006/0208198 A1* | 9/2006 | Harrison | 250/372 |
| 2007/0187627 A1* | 8/2007 | Ershov et al. | 250/504 R |
| 2008/0275658 A1* | 11/2008 | Harvey | 702/81 |
| 2009/0200279 A1* | 8/2009 | Li | 219/121.66 |

* cited by examiner

*Primary Examiner* — Tarifur Chowdhury
*Assistant Examiner* — Michael P Lapage
(74) *Attorney, Agent, or Firm* — James D. Welch

(57) ABSTRACT

A system for and method of mapping process samples which are present in an environmental control chamber at a plurality of "X"-"Y" locations on the surface thereof, wherein the system includes a shield between windows for entering and exiting a beam of electromagnetic radiation, and a process sample.

11 Claims, 6 Drawing Sheets

TO CONTROL OF
ELLIPSOMETER/
POLARIMETER
ELEMENT
OPERATION

SAMPLE MAPPING IN ENVIRONMENTAL CHAMBER

This Application Claims Benefit of Provisional No. 61/191,970 Filed Sep. 15, 2008.

TECHNICAL AREA

The present invention relates to systems and methods for investigating process samples at a plurality of points in an "X"-"Y" plane of the surface thereof, (ie. mapping process samples), using a beam of electromagnetic radiation; and more particularly to a system for and method of mapping process samples which are present in an environmental control chamber, wherein said system comprises a shield between windows for entering said beam of electromagnetic radiation and said process sample.

BACKGROUND

It is known to use various combinations of "X"-"Y" position control means to enable investigating a plurality of locations on a process sample surface with an electromagnetic beam. For instance, a Patent to Finarov No. RE38,153 describes a Two-Dimensional Beam Deflector system. It is also known to process samples in an environmentally controlled chamber and investigate the process sample with an electromagnetic beam through a window. This is exemplified by a Patent to Stehle et al, U.S. Pat. No. 6,687,002. Further, a Patent to Woollam et al., U.S. Pat. No. 6,937,341 describes a system for simultaneously investigating a sample from the top and bottom thereof.

There remains, however, need for improved systems and methods of mapping process samples which are present in an environmentally controlled chamber, using an electromagnetic beam.

DISCLOSURE OF THE INVENTION

The present invention comprises a system for use in mapping process samples while in an environmentally controlled chamber comprising:
  a) an environmental control chamber;
  b) a process sample supporting stage inside said environmental control chamber;
  c) a source and detector of a beam of electromagnetic radiation outside said environmental control chamber; and
  d) at least one material provision source inside said environmental control chamber.

Said process sample supporting stage is capable of an "X" translation motion and said source and detector of a beam of electromagnetic radiation being capable of a "Y" translation. ("X" and "Y" are used to denote an orthogonal relationship and are not to be considered locked into any labratory frame of reference), that is, it is to be understood that "X" and "Y" are used as an example to indicate locating spots on a process sample, and do not imply any orientation in lab coordinates). Further, an "R" "Theta" system can be functionally equivalent.

Said environmental control chamber further comprises windows for entering and exiting said a beam of electromagnetic radiation provided by the source thereof from outside of said environmental control chamber.

In use, before, while or after a process sample present in said environmental control chamber has material deposited thereupon from said at least one material deposition source, or etched therefrom, said process sample can be positioned in an "X" direction while said source and detector of a beam of electromagnetic radiation are simultaneously positioned in a "Y" direction thereby allowing investigation of any of a multiplicity locations on said process sample without removing it from inside said environmental control chamber. It is also within the scope of the present invention to process a sample in one chamber and then move it to a different environmental control chamber section, or a different chamber in the same environmental control chamber, in which said process sample can be positioned in an "X" direction while said source and detector of a beam of electromagnetic radiation are positioned in a "Y" direction, thereby allowing investigation of any of a multiplicity locations on said process sample without removing it from inside said different environmental control chamber. Also, the process sample can be stationary or moving during investigation thereof. Unless specifically limited, the claims are to be interpreted to include any such arrangement.

Importantly, said system is distinguished by the presence of a shield between said windows and said process sample, said shield having at least one opening therein through which said beam of electromagnetic radiation passes in use, the purpose of said shield being to protect said windows against having material deposited thereupon or etched therefrom during use. (Note, The word "material", as regards deposition onto a window can mean either material deposited onto, or material etched from a sample as the material provision source can provide material to be deposited or to effect etching of a process sample).

Further, said windows can be above and/or below the process sample.

The present invention also comprises a method of investigating a process sample inside an environmental chamber at a plurality of points on a surface thereof, to enable mapping of said process sample, said method comprising the steps of:
  a) providing a system for use in mapping process samples as described above;
  b) causing said process sample supporting stage to position said process sample at an "X" translation position;
  c) with the process sample and source and detector so oriented, causing the source to cause a beam of electromagnetic radiation to enter said environmental control chamber, reflect from said process sample surface, and exit said environmental control chamber and enter said detector;
practicing at least one additional step selected from the group consisting:
  d) causing said process sample supporting stage to provide said process sample at a different "X" translation position;
  e) causing said source and detector of a beam of electromagnetic radiation to be provided at a "Y" translation position; and
again causing the source to cause a beam of electromagnetic radiation to enter said environmental control chamber, reflect from said process sample surface, and exit said environmental control chamber and enter said detector.

Said method can further comprise performing at least one selection from the group consisting of:
  storing at least some data provided by said detector in machine readable media;
  analyzing at least some of the data provided by said detector and storing at least some of the results of said analysis in machine readable media;
  displaying at least some data provided by said detector by electronic and/or non-electronic means;

analyzing at least some of the data provided by said detector and displaying at least some of the results of said analysis by electronic and/or non-electronic means;

causing at least some data provided by said detector to produce a signal which is applied to provide a concrete and tangible result; and analyzing at least some of the provided by said data detector and causing at least some thereof to produce a signal which is applied to provide a concrete and tangible result.

Said environmental control chamber can be a single system with a plurality of Chamber sections or alternatively stated, it can be a combination of a plurality of seperate Chamber sections, (which possibilities are to be considered as functionally equivalent), and said process sample can be moved through said sections while practicing step d, or said process sample can be held motionless while practicing step d, in any Chamber section, located before, in or after the environmental control chamber, or section thereof, in which a process sample has material deposited thereupon or etched therefrom.

The present invention will be better understood by reference to the Detailed Description Section of this Specification, in conjunction with the Drawings.

DETAILED DESCRIPTION

Figure 1:
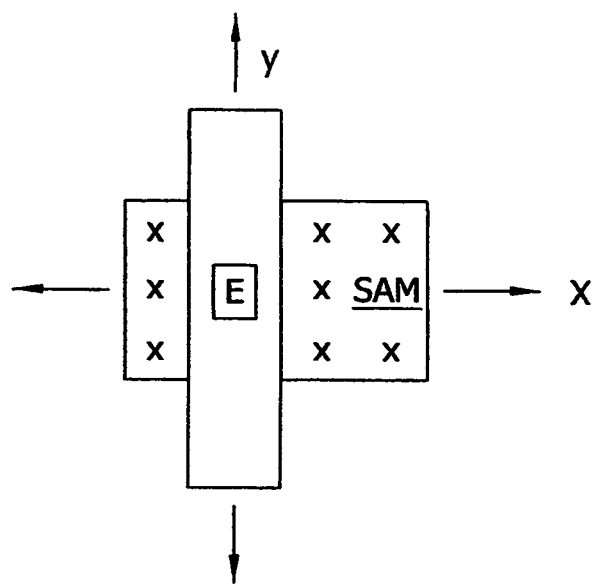
FIG. 1 demonstrates that it is known to map process samples using "X"-"Y" translation effecting means.

Turning now to the Drawings, FIG. 1 demonstrates that process samples can be mapped, (ie. investigated a beam of electromagnetic radiation at a plurality of points on the surface thereof). Note that a Process Sample (SAM) can be caused to move in an "X" direction, while a source of the Beam, (eg. and Ellipsometer (E)), is moved in a "Y" direction.

Figure 2:
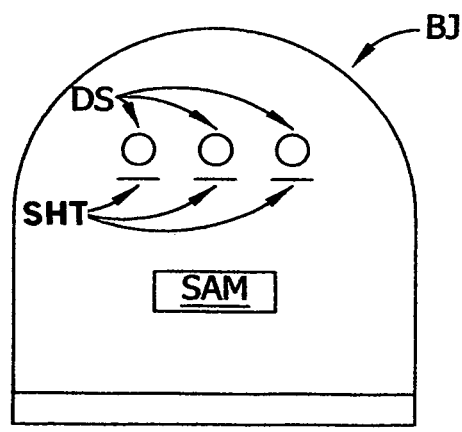
FIG. 2 demonstrates it is known to process a process sample (SAM) in an environmentally controlled chamber (BJ) by causing deposition sources (DS) to provide materials to the process sample (SAM).

FIG. 2 demonstrates it is known to process a Process Sample (SAM) in an Environmentally Controlled Chamber (BJ) by causing Deposition Sources (DS) to provide materials to the Process Sample (SAM). A typical approach is to provide Shutters (SHT) associated with each Deposition Source (DS) which are operated to allow and prevent access to the Process Sample (SAM).

Figure 3:
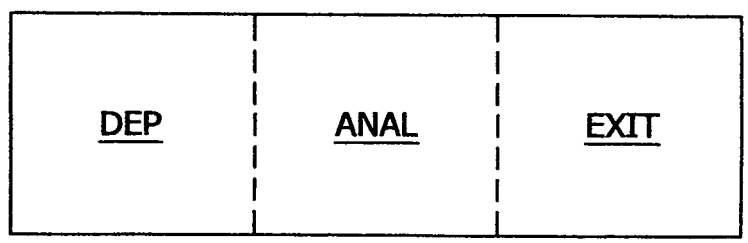
FIG. 3 shows that a process sample (SAM) processing system can be multi-sectional.
Figure 4:
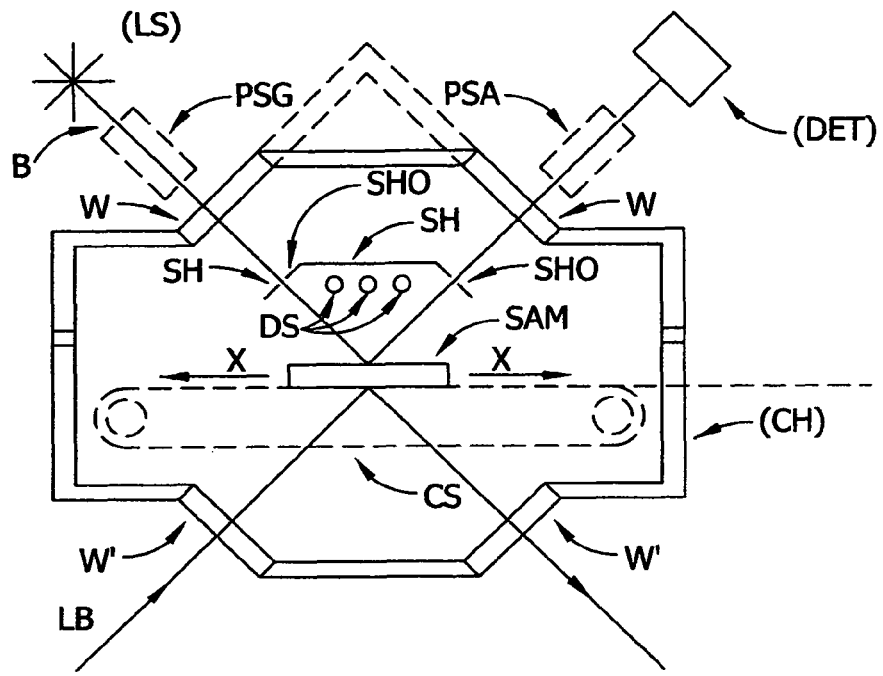
FIGS. 4 and 5 disclose front elevational and top views of a present invention system.
Figure 5:
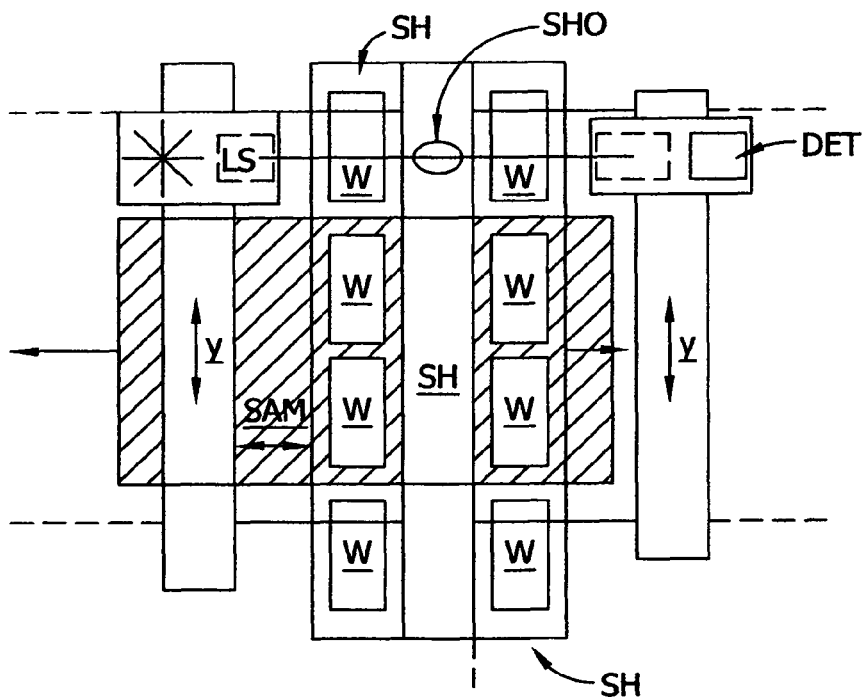

FIG. 3 shows that a Process Sample (SAM) processing system can be multi-sectional and comprise a plurality of chambers. There can be a Deposition Section (DEP), (eg. a FIG. 2 like system), in which a Process Sample (SAM) is processed, with an Analysis Section (ANAL), (eg. a FIG. 1 like system), sequentially following, and with a Process Sample (SAM) Exit Section (EXIT) sequentially following thereafter. Additional sections, such as for use in sample entry, can also be present. Further, while the shown example is most typical, it is to be noted that additional analysis can be performed in chamber sections other than that identified by (Anal). For instance, an ellipsometer can be present in a Sample Deposition/Etching Chamber section as shown in FIGS. 4 and 5, but might instead, or also, be present in a seperate Chamber section as demonstrated by FIG. 3 wherein analysis is not indicated as being performed in a deposition Chamber, but rather an Analysis (ANAL) Chamber which follows a Deposition Chamber. Ellipsometers could, for instance, be mounted to enable investigation of a sample in all three indicated Chambers, (DEP) (ANAL) and (EXIT). FIG. 3 is demonstrative and not limiting in this regard.

FIGS. 4 and 5 disclose a present invention system. FIG. 4 shows a Front Elevational view of an Environmentally Controlled Chamber (CH) which indicates that a Process Sample (SAM) can be mounted to a Conveyor System (CS) inside the Environmentally Controlled Chamber (CH), which enables Process Sample (SAM) motion in a "X" direction. FIG. 5 shows a Top View of the Environmentally Controlled Chamber (CH) which indicates that a Source (LS) of a Beam, (see "B" in FIG. 4), of Electromagnetic Radiation, which is exterior to the Environmentally Controlled Chamber (CH), can be moved in a "Y" direction.

FIG. 4 shows the Beam (B) of electromagnetic Radiation enters the Environmentally Controlled Chamber (CH) through a Window (W), passes through an opening (SHO) in a Shield (SH), reflects from the Process Sample (SAM) and exits through a Window (W). FIG. 4 show said Beam (B) can be, but is not necessarily, polarized by a Polarization State Generator (PSG) and analyzed by a Polarization State Analyzer (PSA) before entering Detector (DET). Note also that FIG. 4 shows Deposition Sources (DS) for providing materials that can deposit on, or etch material from, the Process Sample (SAM) surface and that they are under a Shield (SH). Said Shield (SH) serves to reduce deposition of materials onto the Windows (W) through which the Beam (B) enters and exits. FIG. 5 shows that the Windows (W) can comprise a plurality of sections, but might Just as well be a single elongated Window (W), (eg. see FIG. 6f showing sample (SAM) and stage (STG)) which shows a Window (W) as a Slit (SL).

(Note—while only one Opening (SHO), is shown in the Shield (SH) in FIG. 5, it is within the scope of the Claims to provide a Shield (SH) with a plurlaity of holes therein. In FIG. 5 this would, for instance, provide additional Openings directly below the Opening (SHO) shown).

FIG. 4 also shows that a Beam (LB) can be entered through a Window (W') from under a Process Sample (SAM) and investigate a deposition onto or etching from the top of a transparent Process Sample (SAM) through which it can pass.

The same, or as shown, a different point on a Process Sample (SAM) can be investigated. It is possible to apply both beams simultaneously in practice.

Figure 6A:
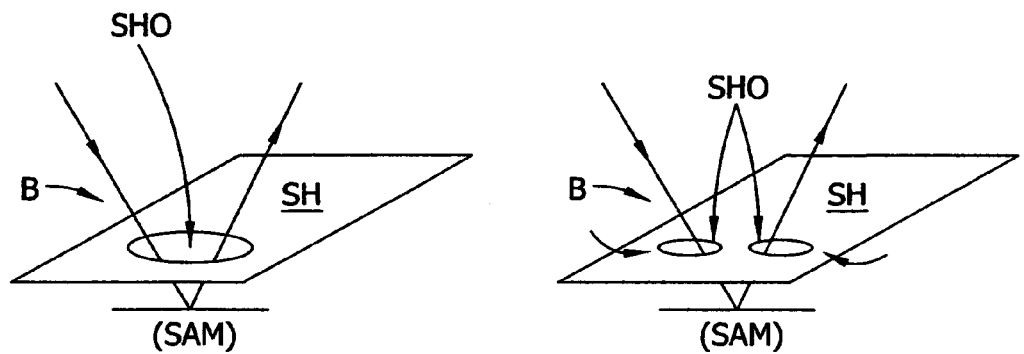
FIG. 6a shows two possible realizations of the shield (SH), (ie. one or two openings (SHO)), through which a beam (B) enters and exits.

FIG. 6a shows a one Opening (SHO) embodiment, which Opening (SHO) can be sufficiently big to allow both incident and reflected Beams (B) to pass therethrough, and a two Opening (SHO) embodiment, one for the incident and one for the exiting Beam (B).

Figure 6B:
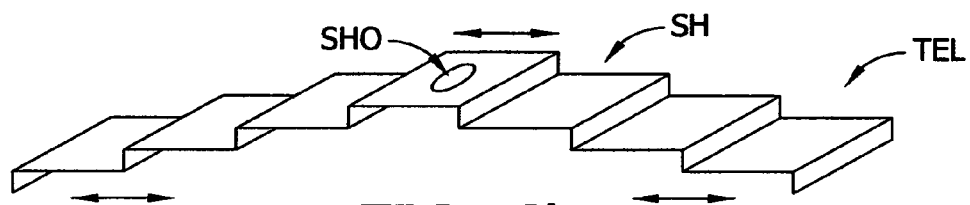
FIGS. 6b, 6c and 6d show that a shield (SH) can have an opening (SHO) which can be moved via telescoping, roller or translation action, respectively.
Figure 6C:
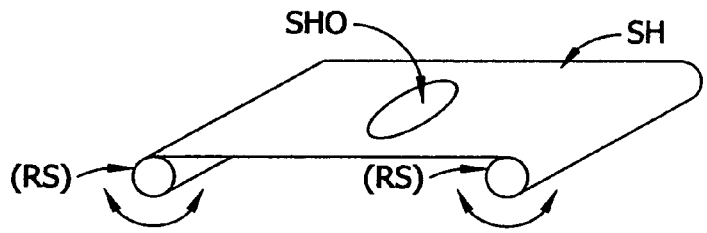
Figure 6D:
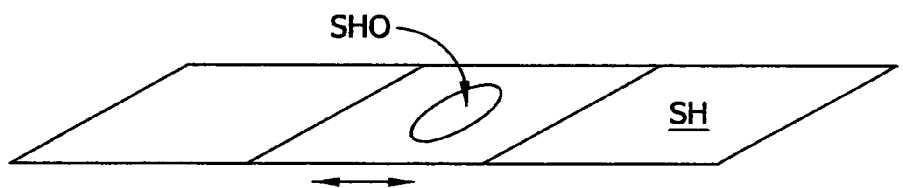

FIGS. 6b and 6c show a Shield (SH) which has an Opening (SHO) which is movable via telescoping (TEL) or a Roller System (RS). FIG. 6d shows a rigid Process Shield (SH) which is simply translatable.

Figure 6E:
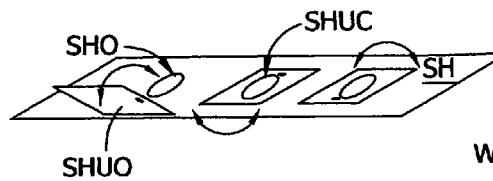
FIG. 6e shows the Shield (SH) can have openings (SHO) which are fitted with Shutters which can be open (SHUO) or closed (SHUC) to control passage of a beam (B) therethrough.
Figure 6F:
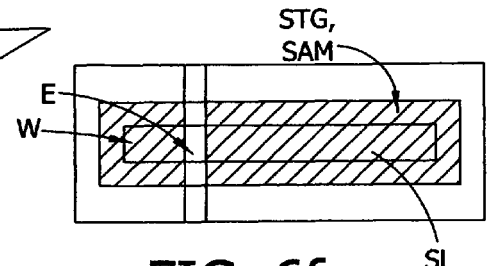
FIG. 6f which shows an entry or exit window (W) can be realized as a slit (SL).

FIG. 6e shows the Openings (SHO) can be fitted with Shutters which can be open (SHUO) or closed (SHUC) to control passage of a Beam (B) therethrough.

Figure 6G:
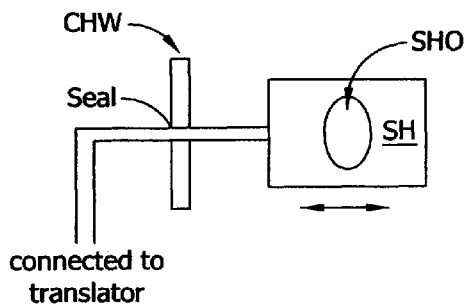
FIG. 6g shows the shield (SH) can be moved by a sealed translator which extends through the chamber (CH) wall (CHW).

FIG. 6g shows the Shield (SH) can be moved by a sealed translator which extends through the Chamber (CH) wall (CHW).

Figure 6H:
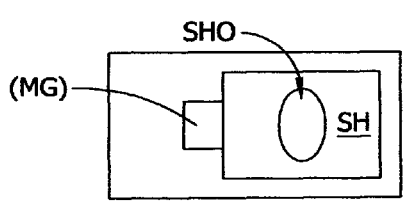
FIGS. 6h and 6i show that a shield (SH) motion can be effected via magnets (MG) which are inside or outside the chamber (CH).
Figure 6I:
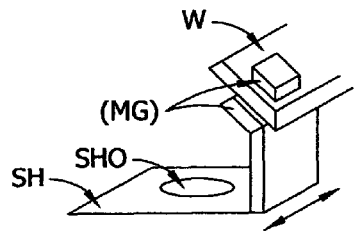
Figure 6J:
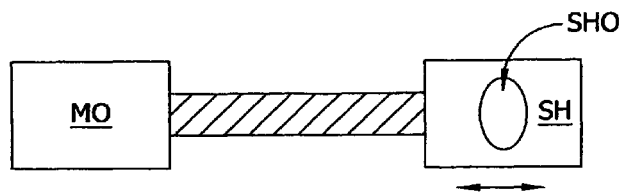
FIG. 6l shows a motor (MO) mounted inside the chamber (CH) can be used to move the shield (SH).

FIGS. 6h and 6i show that Shield (SH) motion can be effected via Magnets (MG) which are positioned inside or outside a Chamber (CH).

Figure 7:
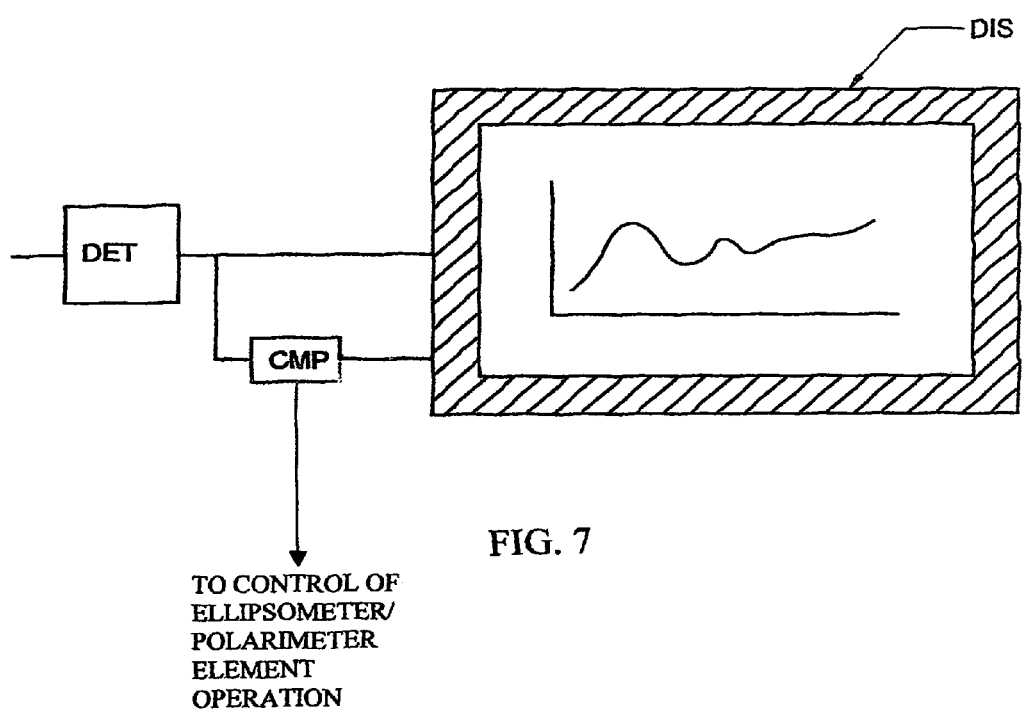
FIG. 7 is included to show that the operation of an ellipsometer can be controlled by a computer.

FIG. 7 is included to show that the operation of an ellipsometer and Sample (SAM) motion can be controlled by a computer (CMP), and that data from the Detector (DET), or analyzed results thereof, can be presented.

Figure 8:
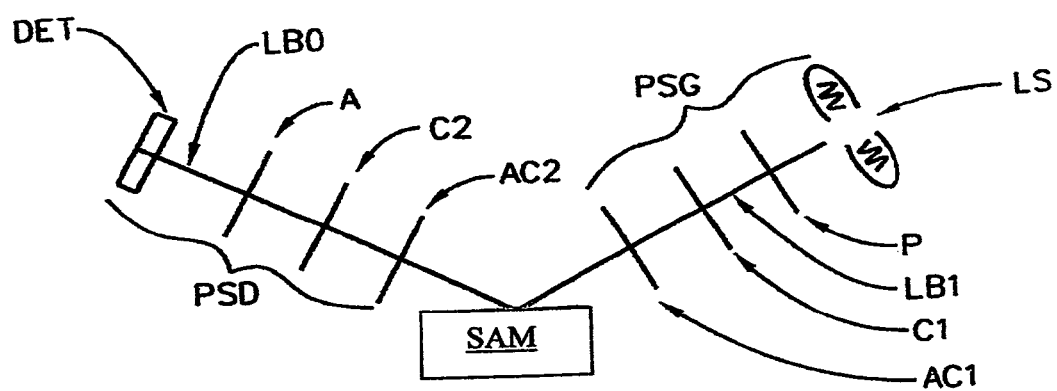
FIG. 8 is included to show the basic elements of an ellipsometer or polarimeter.

FIG. 8 is included to show the basic elements of an ellipsometer or polarimeter. Shown are a source of a beam of electromagnetic radiation (LS), a polarizer (P), a possible first compensator (C1), first possible additional components (AC1), a sample (SS), second possible additional components (AC2), a possible second compensator (C1), an analyzer (A) and a detector (DET). Note a grouping of elements (LS) (P) (C1) and (AC1) are identified as a polarization state generator (PSG) and a grouping of elements (A) (C2) (AC2) and (DET) are identified as a polarization state detector (PSG). Also indicated are input beam (LB1) before the sample (SAM) and output beam (LBO) thereafter.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for use in mapping process samples while in an environmentally controlled chamber comprising:
   a) an environmental control chamber;
   b) a process sample supporting stage inside said environmental control chamber;
   c) a source and detector of a beam of electromagnetic radiation outside said environmental control chamber; and
   d) at least one material deposition source or etchant source inside said environmental control chamber;

said process sample supporting stage being movable in an "X" axis translation direction;
said source and detector of a beam of electromagnetic radiation being movable in a "Y" axis translation direction;
said environmental control chamber further comprising windows for entering and exiting said beam of electromagnetic radiation provided by the source thereof from outside of said environmental control chamber;
such that in use, before, while, or after, a process sample present in said environmental control chamber has material deposited thereupon or etched therefrom by operation of said at least one material deposition source or etchant source, said process sample is sequentially positioned in a plurality of "X" translation direction locations while said source and detector of a beam of electromagnetic radiation are positioned in a plurality of "Y" translation direction locations, thereby allowing investigation of a multiplicity of "X"-"Y" locations on said process sample without removing it from inside said environmental control chamber;
said system being distinguished by the presence of a shield between said windows and said process sample, said shield being closer to said at least one material deposition source or etchant source than to said windows, and not being between said at least one material deposition source or etchant source and said process sample, said shield further having at least one opening therein through which said beam of electromagnetic radiation passes in use, the purpose of said shield being to protect said windows against having material deposited thereupon during use, other than that passing through said at least one opening.

2. A system as in claim 1, wherein the environmental control chamber further comprises at least two material deposition or etchant sources.

3. A system as in claim 1 in which said windows are positioned as a selection from the group consisting of:
   above the process sample;
   below the process sample;
   both above and below the process sample.

4. A system as in claim 1 in which the environmental control chamber comprises a plurality of sub-chambers or sub-sections of a single chamber, and wherein said process sample motion in an "X" translation direction while said source and a beam of electromagnetic radiation motion in a "Y" translation direction are performed in the same environmental control sub-chamber, or sub-section thereof, wherein material deposition or process sample etching is performed.

5. A system as in claim 1 in which the environmental control chamber comprises a plurality of sub-chambers or sub-sections of a single chamber, and wherein said process sample motion in an "X" translation direction while said source and a beam of electromagnetic radiation motion in a "Y" translation direction are performed in a different environmental control sub-chamber, or sub-section thereof, than wherein material deposition or process sample etching is performed.

6. A system for use in mapping process samples while in an environmentally controlled chamber as in claim 1, which further comprises shutters which can be opened or closed to control passage of said electromagnetic radiation through said at least one opening in said shield.

7. A method of investigating a process sample inside an environmental chamber at a plurality of points on a surface thereof to enable mapping of said process sample, comprising the steps of:
   a) providing a system for use in mapping process samples while in an environmentally controlled chamber comprising:
      a') an environmental control chamber;
      b') a process sample supporting stage inside said environmental control chamber;
      c') a source and detector of a beam of electromagnetic radiation outside said environmental control chamber; and
      d') at least one material deposition or etchant source inside said environmental control chamber;
   said process sample supporting stage being movable in an "X" axis translation direction;
   said; source and detector of a beam of electromagnetic radiation being movable in a "Y" axis translation direction;

said environmental control chamber further comprising windows for entering and exiting said beam of electromagnetic radiation provided by the source thereof from outside of said environmental control chamber;

such, that in use, before, while, or after, a process sample present in said environmental control chamber has material deposited thereupon or etched therefrom by operation of said at least one material deposition source or etchant source, said process sample is sequentially positioned in a plurality of "X" translation direction locations while said source and detector of a beam of electromagnetic radiation are positioned in a plurality of "Y" translation direction locations, thereby allowing investigation of a multiplicity of "X"-"Y" locations on said process sample without removing it from inside said environmental control chamber;

said system being distinguished by the presence of a shield between said windows and said process sample, said shield being closer to said at least one material deposition source or etchant source than to said windows, and not being between said at least one material deposition source or etchant source and said process sample, said shield further having at least one opening therein through which said beam of electromagnetic radiation passes in use, the purpose of said shield being to protect said windows against having material deposited thereupon during use, other than that passing through said at least one opening;

b) causing said process sample supporting stage to position said process sample at an "X" translation position;

c) with the process sample and source and detector so oriented, causing the source to cause a beam of electromagnetic radiation to enter said environmental control chamber, reflect from said process sample surface, and exit said environmental control chamber and enter said detector;

practicing at least one additional step selected from the group consisting:

d) causing said process sample supporting stage to provide said process sample at a different "X" translation position;

e) causing said source and detector of a beam of electromagnetic radiation to be provided in a "Y" translation position; and again causing the source to cause a beam of electromagnetic radiation to enter said environmental control chamber, reflect from said process sample surface, and exit said environmental control chamber and enter said detector.

8. A method as in claim 7, wherein said process sample moves while practicing step d or e.

9. A method as in claim 7, wherein said process sample is not in motion while practicing step d or e.

10. A method as in claim 7, wherein the environmental control chamber comprises a plurality of sub-chambers or sub-sections of a single chamber, and wherein said process sample motion in an "X" direction while said source and, a beam of electromagnetic radiation motion in a "Y" direction are, performed in the same environmental control sub-chamber, or sub-section thereof, wherein material deposition or process sample etching is performed.

11. A method as in claim 7, wherein the environmental control chamber comprises a plurality of sub-chambers or sub-sections of a single chamber, and wherein said process sample motion in an "X" direction while said source and a beam of electromagnetic radiation motion in a "Y" direction are performed in a different environmental control sub-chamber, or sub-section thereof, wherein material deposition or process sample etching is performed.

\* \* \* \* \*